United States Patent [19]

Krueger et al.

[11] 4,311,694

[45] Jan. 19, 1982

[54] AMORPHOUS COPRECIPITATES OF 4-(MONOALKYLAMINO) BENZOIC ACID AND DERIVATIVES AND CERTAIN WATER-SOLUBLE MATERIALS

[75] Inventors: James E. Krueger, New City; Eugene A. Carpentier, Spring Valley, both of N.Y.

[73] Assignee: American Cyanamid Company, Stamford, Conn.

[21] Appl. No.: 109,014

[22] Filed: Dec. 31, 1979

[51] Int. Cl.$^3$ .................... A61K 31/70; A61K 31/715
[52] U.S. Cl. ..................................... 424/180; 424/310; 424/319; 424/343; 424/361
[58] Field of Search ............... 424/310, 319, 180, 83, 424/361, 343

[56] References Cited

U.S. PATENT DOCUMENTS

| | | | |
|---|---|---|---|
| 3,200,039 | 8/1965 | Thompson | 424/310 |
| 3,691,281 | 9/1972 | Battista | 424/343 |
| 3,751,277 | 8/1973 | Small et al. | 424/361 |
| 3,868,416 | 2/1975 | Albright et al. | 424/319 |
| 3,962,420 | 6/1976 | Seidel et al. | 424/83 |
| 4,059,686 | 11/1977 | Tanaka et al. | 424/83 |

FOREIGN PATENT DOCUMENTS 2055930  11/1972  Fed. Rep. of Germany .

OTHER PUBLICATIONS

Chion et al., J. Pharmaceutical Sciences, vol. 58, pp. 1505–1509, 1969.

*Primary Examiner*—Blondel Hazel
*Attorney, Agent, or Firm*—Jack W. Richards

[57] ABSTRACT

A composition of matter in pharmaceutical dosage form comprising an amorphous coprecipitate of water-soluble polyhydroxylic organic compounds and 4-(monoalkylamino)-benzoic acid and derivatives for the treatment of atherosclerosis and hyperlipidemia.

9 Claims, No Drawings

AMORPHOUS COPRECIPITATES OF 4-(MONOALKYLAMINO) BENZOIC ACID AND DERIVATIVES AND CERTAIN WATER-SOLUBLE MATERIALS

FIELD OF THE INVENTION

This invention relates to amorphous coprecipitates of 4-(monoalkylamino)benzoic acid and derivatives with polyhydroxylic organic compounds. These amorphous coprecipitates have been found useful as pharmaceutical dosage forms assisting in absorption of the hypolipidemic and anti-atherosclerosis compound 4-(monoalkylamino)benzoic acid and derivatives.

BACKGROUND OF THE INVENTION 4-(monoalkylamino)benzoic acid and derivatives has been found to be an effective pharmaceutical agent in the treatment of atherosclerosis and hyperlipidemia. The general range of effective blood levels of this drug to effect beneficial changes in patient lipid levels is generally in a range from about 1 microgram per ml. to about 10 milligrams per ml. However, a relatively low rate of absorption of this drug across the gut wall has required relatively large oral dosages to be administered for an effective final concentration (Table II). A number of substances have now been found to enhance absorption of 4-(monoalkylamino)benzoic acid and derivatives across the gut wall. These are water-soluble polyhydroxylic organic compounds, non-ionic surfactants, and polyvinylpyrrolidone. Polyvinylpyrrolidone as an augmentor of absorption is the subject of U.S. application Ser. No. 109,010; non-ionic surfactant is the subject of U.S. application Ser. No. 109,015 filed on even date herewith.

PRIOR ART (1) U.S. Pat. No. 3,868,416 (ACCO)
(2) Consecutive ACCO Cases 26,896–26,909
(3) U.S. Pat. No. 3,673,163
(4) P. Molyneux and H. Frank, J.A.C.S., 83, 3169 (1961)
(5) T. Higuchi, et al., J. Am. Pharm. Assoc. Sci. Ed., 43, 393 (1954) and 398 (1954)
(6) M. Mayersohn, et al., J. Pharm. Sci., 55, 1323 (1966)
(7) A. P. Simonelli, et al., J. Pharm. Sci., 58, 538 (1959)
(8) J. P. Davignon, Bull. Parent. Drug Assoc., 28, 83 (1969)

DESCRIPTION OF THE INVENTION

This invention is concerned with a composition of matter comprising a compound of the formula;

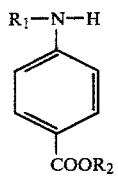

wherein $R_1$ is an unbranched or branched alkyl group $C_nH_{2n+1}$ wherein n is 8 to 19 and $R_2$ is hydrogen, lower alkyl, benzyl, dilower alkylaminoethyl, or lower alkoxyethyl together with the pharmaceutically acceptable salts thereof and watersoluble polyhydroxylic organic compounds such as mono- and di-saccharides (e.g. lactose, sucrose), soluble starches and gums, (e.g. mannan, dextran) and polyglycols (e.g. polyethylene glycol, mannitol, sorbitol) and combinations thereof.

The above described compounds, their use as hypolipidemic agents and conventional pharmaceutical dosage forms for these products are fully disclosed in U.S. Pat. No. 3,868,416, the teachings of which are incorporated herein by reference.

It has now been discovered that a composition of matter comprising an amorphous coprecipitate of one of the aforementioned compounds and water-soluble polyhydroxylic organic compounds, provides a product which, when administered orally to warm-blooded animals, provides for substantially enhanced blood levels of the therapeutic component and substantially reduced serum lipid levels when compared with the oral administration of one of the aforementioned compounds alone.

The above identified coprecipitates are prepared by converting the therapeutic compound to its salt by any convenient means, dissolving said salt to about a 1 to 15% (5–10% preferred) concentration in an aqueous solution containing 1 to 30% (5–10% preferred) water soluble polyhydroxylic organic compound at a temperature of about 50° to 90° C. (65°–75° C. preferred) quick-freezing this solution by immersion in a low temperature bath and lyophilizing. The resulting amorphous coprecipitate is then pulverized and should be in a ratio of drug to carrier of about 1:0.5 to 1:10 with 1:1 to 1:5 preferred.

The coprecipitates of this invention are administered to warm-blooded animals in amounts ranging from 5 mg. to about 200 mg. (based on the active component, polyalkylaminobenzoic acid sodium salt content) per kilogram of both weight per day. A preferred dosage regimen for optimum results is from about 5 mg. to about 50 mg. mg. (of active component) per kilogram of body weight per day, and such dosage units are employed that a total of from about 350 mg. to about 3.5 g. of the active component for a subject of about 70 kg. of body weight are administered in a 24 hour period. This dosage regimen is adjusted to provide the optimum therapeutic resonse, and it is stressed that the essence of the invention lies not in any specific dosage level but in the enhanced absorption of polyalkylamino benzoic acid.

For example, in one regimen several divided doses are administered daily or in another the dose is proportionally reduced as indicated by the exigencies of the situation. A decided practical advantage of this invention is that the coprecipitate is administered in any convenient manner such as the oral or buccal routes or it is incorporated directly in the diet with good uptake.

The coprecipitate of the present invention is orally administered, for example, with an inert diluent or with an assimilable edible carrier, or enclosed in hard shell gelatin capsules, or compressed into tablets, or incorporated in the diet. For oral therapeutic administration, the coprecipitate is incorporated with excipients and used in the form of ingestible tablets, buccal tablets, troches, capsules, and the like. Such compositions and preparations contain at least 0.1% of active component. The ratio of the active component in the compositions and preparations are varied and conveniently between about 1:0.5 to about 1:10 as to coprecipitate. The amount of active component in such therapeutically useful compositions is such that a suitable dosage will be obtained.

In some forms the tablets, troches, pills, capsules and the like also contain the following: A binder such as gum tragacanth, acacia, corn starch or gelatin; excipients such as potato starch, alginic acid and the like; a lubricant such as magnesium stearate; and a sweetening agent such as sucrose or saccharin or a flavoring agent such as peppermint, oil of wintergreen, or cherry flavoring. One dosage unit of capsule form contains, in addition to materials of the above type, a liquid carrier. Note that such carrier must be a non-solvent for the coprecipitate. In some embodiments various other materials are present as coatings, or to otherwise modify the physical form of the dosage unit. For instance, tablets, pills or capsules are coated with shellac, sugar or both. Any material used in preparing any dosage unit form is pharmaceutically pure and substantially non-toxic in the amounts employed.

The water-soluble polyhydroxylic organic compounds form coprecipitates with polyalkylaminobenzoic acid sodium salt and other free salts as well as the acid form which promotes absorption of the active component thus enhancing bioavailability.

The following tests were performed. The coprecipitates of this invention were compared with p-hexadecylaminobenzoic acid sodium salt by the following procedures. These tests and the examples following are merely illustrative of this invention and in no way limiting. This invention will be limited solely by the claims.

Normal and $^{14}$C-labelled p-hexadecylaminobenzoic acid sodium salt was formed as amorphous coprecipitates with various water-soluble polyhydroxylic organic compounds at varying concentrations, according to the procedures given in the following examples and filled in hard shell gelatin capsules. Each capsule contained 110 mg. of normal or $^{14}$C-labeled p-hexadecylaminobenzoic acid sodium salt or 200 mg. of normal p-hexadecylaminobenzoic acid sodium salt.

Control capsules were prepared by mixing and spatulating for 5 minutes 1.320 g. of normal or $^{14}$C-labeled p-hexadecylaminobenzoic acid sodium salt, 1.776 g. of lactose monohydrate and 64.8 mg. of modified starch. About 0.5 ml. of water was added dropwise with mixing to form granules, which were then dried at 50° C. for 18 hours. The granules were passed through a No. 17 sieve, 32.4 mg. of sodium lauryl sulfate and 32.4 mg. of magnesium stearate were passed through the sieve and mixed with the granules by spatulation for 3 minutes and then filled in hard shell gelatin capsules as described above.

The particle size of all coprecipitates was qualitatively similar.

The capsule formulations were administered orally to dogs by hand insertion. The dogs were purebred male beagles from Marshall Research Animals Inc., North Rose, New York. All dose administrations were followed by a 30 ml. water wash.

The capsule formulations were administered orally to monkeys by use of a balling gun. The monkeys were male and female Cynologus (*Macaca Fascicularis*) monkeys from Primate Imports, Port Washington, N.Y. All dose administrations were followed by a 2 ml. wash of grape juice.

All animals had free access to water at all times. They were fed in the morning of the days preceding and following the day of drug administration. Half of the monkeys in the comparative fed vs. fasted study were fed their normal diet one hour prior to drug administration. For those studies in which blood was collected, the animals were not fed again until after the 23 or 24 hour blood samples were collected.

Each dog was fed 300 g. of Respond 2000 ™ dog food (Agway Country Foods, Waverly, N.Y.) daily.

On the days of feeding the monkeys were provided Purina Monkey Chow (Ralston Purina Co., St. Louis, Mo.) in the morning and given bread and fruit in the afternoon.

The dogs were housed in individual cages designed to collect the voided urine separately from the feces. The urine was collected at room temperature in individual two liter polyethylene containers. The collection pans were washed with 50–100 ml. of water after each urine collection and each rinse was added to the respective daily collection or urine.

Blood samples were obtained from the monkeys from the femoral artery and injected immediately into 10 ml. Corvac ® tubes and allowed to clot. The tubes were centrifuged and the sera were pipetted directly into both counting vials and acid-washed conical tubes. The samples for the fluorometric analysis were frozen until analyzed.

The radioactivity measurements were made as follows: All samples were counted in 10 ml. 3a70B phosphor (Research Products International Corp.) using a Beckman LS9000 Liquid Scintillation Spectrophotometer. Two drops of saturated aqueous ascorbic acid solution were added to each sample to minimize chemiluminescence. Conversion to absolute radioactivity was performed by use of an internal computer synthesized channels ratio calibration curve based on sealed quenched carbon-14 standards.

Daily urine collection samples of less than one liter were diluted to one liter with water and mixed. Urine samples of one ml. each were counted in either triplicate or quadruplicate for each time period. Single and duplicate 0.5 ml. serum samples were analyzed. One-half ml. of water was added to each serum-containing vial to prevent gel separation of the final counting mixture.

The serum samples were assayed by a fluorometric method as follows: Aliquot volumes of from 0.1 to 0.5 ml. were analyzed. For samples of less than 0.5 ml., water was added to bring the volume to 0.5 ml. The samples were transferred to acid washed 15 ml. glass stoppered centrifuge tubes and 0.4 ml. of water and 0.5 ml. of freshly prepared 4% potassium hydroxide in 95% ethanol were added. The contents were mixed on a vortex mixer, stoppered and heated for 75 minutes at 95° C., then cooled to room temperature. A 3.5 ml. portion of water:acetic acid (4:3) was added and the contents were mixed. Eight ml. of hexane containing 3% isoamyl alcohol was added, the contents were shaken vigorously and then centrifuged. A 3 ml. portion of the organic layer was transferred to a cuvette and the fluorescence was measured on a Perkin-Elmer Model 1000 fluoroescence Spectrophotometer equipped with a constant voltage power supply; Excitation:300 nm. Oriel interference filter; Emission:339 nm. Perkin-Elmer interference filter, mirrored side facing sample compartment, narrow slit width, scale expansion knob turned fully counter-clockwise. The results were compared to a standard curve plotted from results obtained in the same manner using samples of $^{14}$C-labeled 4-(hexadecylamino)benzoic-carboxy-$^{14}$-C-acid, 2,3-dihydroxypropyl ester.

The results of these tests appear in the following tables.

TABLE I

Summary of the Urinary Excretion Data from Bioavailability Studies in Fasted Dogs Expressed in Percent of Administered Dose

| Compound | Dog No. | Weight (kg.) | Dose (mg./kg.) | Urinary Excretion (% of Dose)* Time in hours | | | | | |
|---|---|---|---|---|---|---|---|---|---|
| | | | | 0–24 | 24–48 | 48–72 | 72–96 | 0–96 | 0–384 |
| Control Capsule | 20758 | 7.4 | 14.7 | 5.1 | 2.0 | 2.1 | 0.7 | 9.9 | 12.8 |
| | 20767 | 9.8 | 11.1 | 4.9 | 2.3 | 1.1 | 0.4 | 8.7 | 11.9 |
| | 20779 | 8.3 | 13.1 | 8.2 | 5.2 | 5.6 | 2.4 | 21.4 | 30.0 |
| | 20797 | 9.1 | 11.9 | 6.1 | 3.3 | 1.5 | 0.9 | 11.8 | 16.4 |
| | 24521 | 9.2 | 12.5 | 6.3 | 3.2 | 1.5 | 0.8 | 11.8 | 16.2 |
| | 24523 | 9.4 | 12.3 | 7.0 | 6.1 | 2.5 | 1.3 | 16.9 | 23.6 |
| Coprecipitate Capsule [Lactose:Drug (3:1)] | 24525 | 7.3 | 15.8 | 8.3 | 11.2 | 8.8 | 2.6 | 30.9 | 45.2 |
| | 20774 | 8.6 | 13.4 | 14.4 | 6.8 | 3.5 | 1.2 | 25.9 | 30.7 |

*Represents percentage of $^{14}$C-labeled drug excreted in urine.

TABLE II

Summary of the Mean 0–96 Hour Urinary Excretion Data from Bioavailability Studies in Fasted Dogs

| Compound | No. of Dogs | Mean Dose (mg./kg.) | Mean Percent of Dose in 0–96 Hour Urine |
|---|---|---|---|
| Control Capsule | 4 | 12.7 | 13.0 |
| Coprecipitate Capsule [Lactose:Drug (3:1)] | 4 | 13.5 | 21.4 |

TABLE III

Summary of Serum Drug Concentrations Determined by Radiometric and Fluorometric Assays from Bioavailability Studies in Fasted Monkeys

| Compound | Unique Animal No. | Sex | Weight (kg.) | Dose (mg./kg.) | mcg. of Drug equivalents/ml. of serum Fluorometric results in parenthesis | | | | | | | 0–48 Hr. AUC* |
|---|---|---|---|---|---|---|---|---|---|---|---|---|
| | | | | | Time in Hours | | | | | | | |
| | | | | | 2 | 4 | 6 | 10 | 14 | 23 | 48 | |
| | 18631 | M | 5.35 | 20.8 | 4.8 | 2.2 | 1.2 | 0.7 | 0.4 | 0.3 | 0.1 | 29.6 |
| | | | | | (3.7) | (1.6) | (0.9) | (0.5) | (0.2) | (0.1) | (0.0) | (18.6) |
| | 23130 | M | 3.25 | 34.3 | 3.6 | 1.4 | 0.7 | 0.4 | 0.3 | 0.3 | 0.1 | 22.2 |
| | | | | | (3.3) | (1.1) | (0.5) | (0.2) | (0.1) | (0.1) | (0.0) | (13.5) |
| | 18723 | F | 2.45 | 45.5 | 9.4 | 11.1 | 4.3 | 2.3 | 1.4 | 0.9 | 0.2 | 90.6 |
| | | | | | (3.7) | (9.2) | (3.5) | (1.8) | (1.0) | (0.4) | (0.1) | (58.9) |
| Control Capsule | mean | | | | 5.9 | 4.9 | 2.1 | 1.1 | 0.7 | 0.5 | 0.1 | |
| | | | | | (3.6) | (4.0) | (1.6) | (0.8) | (0.4) | (0.2) | (0.0) | |
| Coprecipitate Capsule [Polyethylene glycol 4000:Drug (1:1)] | 18633 | M | 4.55 | 27.2 | 5.2 | 2.8 | 1.8 | 1.0 | 0.5 | 0.3 | 0.1 | 35.2 |
| | | | | | (4.2) | (1.9) | (1.3) | (0.7) | (0.3) | (0.1) | (0.0) | (21.9) |
| | 20125 | M | 2.65 | 46.7 | 2.7 | 8.9 | 10.6 | 9.6 | 7.3 | 4.1 | 0.3 | 216.5 |
| | | | | | (2.0) | (5.8) | (7.2) | (7.6) | (5.7) | (3.2) | (0.1) | (161.2) |
| | 18718 | F | 2.60 | 47.6 | 8.4 | 2.6 | 1.3 | 0.9 | 0.5 | 0.6 | 0.2 | 45.8 |
| | | | | | (5.8) | (1.7) | (0.9) | (0.5) | (0.2) | (0.3) | (0.0) | (27.2) |
| | mean | | | | 5.4 | 4.8 | 4.6 | 3.8 | 2.8 | 1.7 | 0.2 | |
| | | | | | (4.0) | (3.1) | (3.1) | (2.9) | (2.1) | (1.2) | (0.0) | |

*AUC = Area under the serum drug concentration-time curve (in mcg.-hr./ml.)

TABLE IV

Summary of Serum Drug Concentrations Determined by the Fluorometric Assay Method from the Bioavailability Study in Fasted and Fed Monkeys

| Compound | Animal No. | Sex | Weight (kg.) | Dose (mg./kg.) | Percent Food Consumption | | Time in Hours (mcg./ml.) | | | | | | | 0–48 Hr. AUC |
|---|---|---|---|---|---|---|---|---|---|---|---|---|---|---|
| | | | | | Time of Dosing | 5 Hours Post Dose | 0 | 2 | 4 | 6 | 10 | 14 | 24 | 48 | |
| | 18631* | M | 5.70 | 37.1 | 100* | 100 | 0.0 | 1.0 | 2.5 | 2.7 | 4.1 | 1.9 | 3.0 | 0.3 | 99.4 |
| | 23130* | M | 3.85 | 54.9 | 20 | 85 | 0.0 | 1.1 | 5.4 | 3.3 | 1.4 | 1.3 | 0.5 | 0.1 | 47.3 |
| | 23206* | F | 2.70 | 78.3** | 5 | 20 | 0.0 | 2.3 | 1.5 | 1.2 | 0.6 | 0.2 | 0.1 | 0.1 | 17.9 |
| | 20098 | M | 5.00 | 42.3 | — | — | 0.0 | 2.3 | 3.0 | 1.8 | 0.8 | 0.5 | 0.3 | 0.0 | 27.8 |
| Control Capsule | 23116 | M | 3.95 | 53.5 | — | — | 0.0 | 7.2 | 5.2 | 2.9 | 1.3 | 0.6 | 0.4 | 0.0 | 49.7 |
| | 18723 | F | 2.70 | 78.3 | — | — | 0.0 | 17.9 | 7.1 | 4.0 | 3.3 | 1.3 | 0.4 | 0.2 | 93.5 |
| Coprecipitate Capsule [Lactose:Drug (3:1)] (2 capsules/- | 20095* | M | 4.70 | 42.6 | 90* | 90 | 0.0 | 2.3 | 1.1 | 1.8 | 3.0 | 2.5 | 4.3 | 0.3 | 118.4 |
| | 23122* | M | 4.20 | 23.8** | 5 | 10 | 0.0 | 2.1 | 1.8 | 1.3 | 2.6 | 0.8 | 0.2 | 0.0 | 31.1 |
| | 23161* | M | 4.00 | 50.0 | 0 | 30 | 0.0 | 0.0 | 0.3 | 2.1 | 1.9 | 2.6 | 3.3 | 0.4 | 93.6 |
| | 20123 | M | 4.50 | 44.4 | — | — | 0.0 | 5.6 | 2.2 | 1.0 | 0.8 | 0.3 | 0.2 | 0.0 | 27.3 |
| | 23124 | M | 4.35 | 46.0 | — | — | 0.0 | 1.5 | 1.9 | 1.7 | 1.1 | 0.5 | 0.3 | 0.0 | 24.9 |

TABLE IV-continued
Summary of Serum Drug Concentrations Determined by the Fluorometric
Assay Method from the Bioavailability Study in Fasted and Fed Monkeys

| Compound | Animal No. | Sex | Weight (kg.) | Dose (mg./kg.) | Percent Food Consumption Time of Dosing | Percent Food Consumption 5 Hours Post Dose | Time in Hours (mcg./ml.) 0 | 2 | 4 | 6 | 10 | 14 | 24 | 48 | 0–48 Hr. AUC |
|---|---|---|---|---|---|---|---|---|---|---|---|---|---|---|---|
| monkey) | 20131 | F | 3.00 | 66.7 | — | — | 0.0 | 0.0 | 0.7 | 1.3 | 0.9 | 1.6 | 0.4 | 0.0 | 26.9 |

*Fed one hour prior to dose administration.
**One capsule requrgitated, not redosed.

The preparation of the coprecipitate of this invention is further illustrated by the following non-limiting examples.

Other such examples will immediately occur to those skilled in the art without departing from the invention.

For example it will be understood that solid water-soluble non-toxic compounds with two or more hydroxylic groups such as sugars, soluble starches, solid polyglycols, polyvinyl alcohols, vegetable and animal gums fall within the class of agents suitable for coprecipitating with polyalkylaminobenzoic acid and salts thereof that will increase the bioavailability of the dry dosage levels.

The invention is limited only by the claims.

EXAMPLE 1

Lactose-p-hexadecylaminobenzoic acid sodium salt (1:3) coprecipitate

A solution of 1.0 g. of p-hexadecylaminobenzoic acid sodium salt and 3.0 g. of lactose in 12.5 ml. of water at 75°–85° C. is frozen quickly by immersion in a −80° C. bath and lyophilized. The resulting solid coprecipitate is pulverized. This coprecipitate is soluble in water at 10 mg./ml. as opposed to p-hexadecylaminobenzoic acid sodium salt, which is soluble in water at 1 mcg./ml.

Coprecipitates containing weight ratios (drug:lactose) of 1:2 and 1:1 may be prepared in the same manner and show similar properties.

EXAMPLE 2

Dextrose-p-hexadecylaminobenzoic acid sodium salt (1:1) coprecipitate

A solution of 1.0 g. of p-hexadecylaminobenzoic acid sodium salt and 1.0 g. of dextrose in 12.5 ml. of water at 75–85° C. is frozen quickly by immersion in a −80° C. bath and lyophilized. The resulting solid coprecipitate is pulverized, providing an amorphous, water-soluble product.

Coprecipitates containing weight ratios (drug:dextrose) of 1:3 and 1:2 may be prepared by the above method and show similar properties.

EXAMPLE 3

Polyethylene glycol-p-hexadecylaminobenzoic acid sodium salt (1:3) coprecipitate A solution of 1.0 g. of p-hexadecylaminobenzoic acid sodium salt and 3.0 g. of polyethylene glycol 4000 in 12.5 ml. of water at 75°–85° C. is frozen quickly by immersion in a −80° C. bath and lyophilized. The resulting solid coprecipitate is pulverized, providing an amorphous, water soluble product.

Coprecipitates containing weight ratios (drug:polyethylene glycol) of 1:2 and 1:1 and in which polyethylene glycol [PEG] 2000 to 6000 may be substituted, may be prepared by the above method and show similar properties.

EXAMPLE 4

Comparative Water Solubility of Precipitates

Aqueous solutions of various coprecipitates were prepared to contain 1 mg./ml. of p-hexadecylaminobenzoic acid sodium salt and the amount of active drug in solution was determined after 1 and 30 minutes. The results appear below:

| Coprecipitate Matrix Material | Weight Ratio Matrix:Drug | % p-Hexadecylaminobenzoic acid Sodium Salt in Solution After 1 minute | After 30 minutes |
|---|---|---|---|
| Lactose | 1:1 | 76–90 | 32–57 |
| Lactose | 2:1 | 96 | 16 |
| Lactose | 3:1 | 90–99 | 12–92 |
| PEG 4000 | 1:1 | 89–90 | 37–38 |
| None | | 4 | 2 |

EXAMPLE 5

Formula for Preparation of Compressed Tablet

| Ingredient | mg./Tablet |
|---|---|
| Active coprecipitate | 0.5–500 |
| Dibasic calcium phosphate NF | qs |
| Starch USP | 40 |
| Modified starch | 10 |
| Magnesium stearate USP | 1–5 |

EXAMPLE 6

Formula for Preparation of Hard Shell Capsule

| Ingredient | mg./Capsule |
|---|---|
| Active coprecipitate | 0.5–500 |
| Lactose, spray dried | qs |
| Magnesium stearate | 1–10 |

We claim:

1. An amorphous coprecipitate providing for substantially enhanced blood levels of a hypolipidemic and anti-atherosclerotic compound consisting essentially of a hypolipidemic and anti-atherosclerotic effective amount of a compound selected from those of the formula:

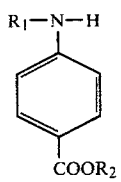

wherein $R_1$ is an unbranched or branched alkyl group $C_nH_{2n+1}$ wherein n is 8 to 19 and $R_2$ is selected from the group consisting of hydrogen, lower alkyl, benzyl, di-lower alkylaminoethyl and lower alkoxyethyl together with the pharmaceutically acceptable salts thereof and a coprecipitating amount of a pharmaceutically acceptable water-soluble polyhydroxylic organic compound selected from the group consisting of mono. and di-saccharides, starches, gums and polyglycols or combination thereof.

2. The amorphous coprecipitate of claim 1 wherein the compound to polyhydroxylic organic compound ratio is about 1:0.5 to 1:10.

3. The amorphous coprecipitate of claim 2 wherein the ratio is about 1:1 to 1:5.

4. The composition of claim 1 or 2 or 3 wherein the water-soluble polyhydroxylic organic compound is a sugar.

5. The composition of claim 4 wherein the sugar is lactose.

6. The composition of claim 4 wherein the sugar is dextrose.

7. The composition of claim 1 or 2 or 3 wherein the water-soluble polyhydroxylic organic compound is a glycol.

8. The composition of claim 7 wherein the glycol is polyethylene glycol.

9. The method of treating hyperlipidemia and atherosclerosis in warm-blooded animals by providing for substantially enhanced blood levels of a hypolipidemic and anti-atherosclerotic compound comprising administering to said animal an amorphous coprecipitate consisting essentially of a hypolipidemic and anti-atherosclerotic effective amount of a compound selected from those of the formula:

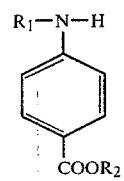

wherein $R_1$ is an unbranched or branched alkyl group $C_nH_{2n+1}$ wherein n is 8 to 19 and $R_2$ is selected from the group consisting of hydrogen, lower alkyl, benzyl, di-lower alkylaminoethyl and lower alkoxyethyl together with the pharmaceutically acceptable salts thereof and a coprecipitating amount of a pharmaceutically acceptable water-soluble polyhydroxylic organic compound selected from the group consisting of mono- and di-saccharides, starches, gums and polyglycols or combination thereof.

* * * * *